US00PP10375P

United States Patent [19]

Glicenstein

[11] Patent Number: Plant 10,375

[45] Date of Patent: May 5, 1998

[54] CHRYSANTHEMUM PLANT NAMED 'ARABELLA'

[75] Inventor: Leon Glicenstein, Salinas, Calif.

[73] Assignee: Yoder Brothers, Inc., Barberton, Ohio

[21] Appl. No.: 702,296

[22] Filed: Aug. 19, 1996

[51] Int. Cl.[6] ..... A01H 5/00

[52] U.S. Cl. ..... Plt./78

[58] Field of Search ..... Plt./78

[56] References Cited

U.S. PATENT DOCUMENTS

P.P. 7,407 12/1990 VandenBerg ..... Plt./78

OTHER PUBLICATIONS

UPOV-ROM Plant Variety Database 1997/01. GTI. Cultivar Name 'Arabella'.

*Primary Examiner*—Howard J. Locker

*Attorney, Agent, or Firm*—Foley & Lardner

[57] ABSTRACT

A Chrysanthemum plant named Arabella particularly characterized by its flat capitulum form; spooned-decorative capitulum type; yellow ray floret color; diameter across face of capitulum of 76 to 83 mm when fully opened; flowering response in Salinas under normal temperatures is 52 to 53 days after start of short days; Flowering response in Bogotá, Colombia is 60 to 68 days after start of short days; plant height is 85 to 91 cm when grown in Salinas with 11 to 18 long days prior to start of short days; height is 89 to 107 cm when grown in Bogotá, Colombia with 21 long days prior to start of short days; peduncle length of the first and the fourth laterals at flowering after removing the apical bud is 10 to 13 cm and 13 to 15 cm when grown in Salinas, Calif.; peduncle length of the first and fourth lateral in Bogotá, Colombia is 10 to 15 cm and 15 to 20 cm, respectively; uniform flowering in year round flowerings in both Salinas, Calif. and in Bogotá, Colombia.

3 Drawing Sheets

The present invention comprises a new and distinct cultivar of Chrysanthemum, botanically known as *Dendranthema grandiflora*, and referred to by the cultivar name Arabella.

Arabella, identified as 3285 (92-L172002), was originated from a cross made by Leon Glicenstein in a controlled breeding program in Salinas, Calif., in 1992.

The female parent of Arabella was the cultivar identified as Momento, disclosed in U.S. Plant Pat. No. 7,407, and described as a flat decorative cut mum with a yellow ray floret color.

The male parent of Arabella was an unnamed seedling, identified as 6597 (86-379001) and described as a yellow-bronze pot mum with a quilled decorative flower type and a diameter of capitulum of 105 to 108 mm when grown as a pinched disbudded pot mum.

Arabella was discovered and selected as one flowering plant within the progeny of the stated cross by Leon Glicenstein in May 1993, in a controlled environment in Salinas, Calif.

The first act of asexual reproduction of Arabella was accomplished when vegetative cuttings were taken from the initial selection in July of 1993 in a controlled environment in Salinas, Calif., by technicians working under supervsion of Leon Glicenstein.

Horticultural examination of controlled flowerings of successive plantings has shown that the unique combination of characteristics as herein disclosed for Arabella are firmly fixed and are retained through successive generations of asexual reproduction. Arabella has not been observed under all possible environmental conditions. The phenotype may vary significantly with variations in environment such as temperature, light intensity and daylength, without, however, any variance in genotype.

The following observations, measurements and comparisons describe plants grown in Salinas, Calif., and near Bogot á, Colombia, South America under greenhouse conditions which approximate those generally used in commercial greenhouse practice.

The following traits have been repeatedly observed and are determined to be basic characteristics of Arabella, which, in combination, distinguish this Chrysanthemum as a new and distinct cultivar:

1. Flat capitulum form.
2. Spooned-decorative capitulum type.
3. Yellow ray floret color.
4. Diameter across face of capitulum of 76 to 83 mm when fully opened.
5. Flowering response in Salinas under normal temperatures is 52 to 53 days after start of short days; flowering response in Bogotá, Colombia is 60 to 68 days after start of short days.
6. Plant height is 85 to 91 cm when grown in Salinas with 11 to 18 long days prior to start of short days; height is 89 to 107 cm when grown in Bogotá, Colombia with 21 long days prior to start of short days.
7. Peduncle length of the first and the fourth laterals at flowering after removing the apical bud is 10 to 13 cm and 13 to 15 cm when grown in Salinas, Calif. Peduncle length of the first and fourth lateral in Bogotá, Colombia is 10 to 15 cm and 15 to 20 cm, respectively.
8. Uniform flowering in year round flowerings in both Salinas, Calif. and in Bogotá, Colombia.

The accompanying photographic drawings show typical inflorescence and leaf characteristics of Arabella, with the colors being as nearly true as possible with illustrations of this type.

Sheet 1 is a color photograph of Arabella grown as a single stem spray cut mum.

Sheet 2 is a black and white photograph of three views of the inflorescence of Arabella.

Sheet 3 is a black and white photograph showing the upper and under sides of the leaves of Arabella at 3 stages of development (mature, intermediate and immature). In sheets 2 and 3 a measuring tape in centimeters has been added.

Of the commercial cultivars known to the inventor, the most similar in comparison to Arabella is the parent cultivar Momento. Reference is made to attached Chart A, which compares certain characteristics of Arabella with the same characteristics of Momento. Similar traits are capitulum form, ray floret color, flowering response to short days in Salinas, Calif., and uniform flowering in year round flowerings in Salinas, Calif. Arabella has a spooned-decorative capitulum type, while Momento has a decorative capitulum type. Arabella has a larger diameter of capitulum, a shorter plant height, thus needing more long days to reach commercial plant height than Momento, and shorter peduncles than Momento, when grown in Salinas, Calif. Since both cultivars have been tested with different long days, no direct comparison of plant height with the same number of long days is available. In addition, Arabella shows uniform flowerings in Bogoté, Colombia, while Momento cannot be grown under the night temperatures prevalent in Bogotá, Colombia, which can be as low as 5 to 8 degrees Celsius.

In the following description color references are made to The Royal Horticultural Society Colour Chart. The color values were determined on plant material grown as a single stem spray cut mum in Salinas, Calif. on Jun. 13, 1996.

Classification

*Botanical.*—*Dendranthema grandiflora* cv Arabella.

*Commercial.*—Flat spooned-decorative spray cut mum.

Inflorescence

A. Capitulum:

*Form.*—Flat.

*Type.*—Spooned-decorative.

*Diameter across face.*—76 to 83 mm when fully opened.

B. Corolla of ray florets:

*Color (general tonality from a distance of three meters).*—Yellow.

*Color (upper surface).*—5A.

*Color (under surface).*—6 C.

*Shape.*—Spooned, with corolla tube of medium length, longitudinal section of outer ray florets straight.

C. Corolla of disc florets:

*Color (mature).*—Closest to 14A.

*Color (immature).*—Closest to 144A.

D. Reproductive organs:

*Androecium.*—Present on disc florets only; scant to no pollen.

*Gynoecium.*—Present on both ray and disc florets.

Plant

A. General appearance:

*Height.*—85 to 91 cm when grown in Salinas with 11 to 18 long days prior to start of short days; height is 89 to 107 cm when grown in Bogotá, Colombia with 21 long days prior to start of short days.

B. Foliage:

*Color (upper surface).*—147A.

*Color (under surface).*—147B.

*Shape.*—Deeply lobed and serrated.

CHART A

COMPARISONS MADE OF PLANTS GROWN AS SINGLE STEM SPRAY CUT MUMS OM SALINAS, CALIFORNIA AND IN BOGOTA, COLOMBIA

| CHARACTERISTICS | ARABELLA | MOMENTO |
|---|---|---|
| Ray floret color | Yellow | Yellow |
| Capitulum form | Flat | Flat |
| and type | Spooned-decorative | Decorative |
| Diameter across face | 76 to 83 mm | 70 to 76 mm |
| of capitulum | | |
| Flowering response | | |
| in Salinas | 52 to 53 days | 51 to 54 days |
| in Bogotá | 60 to 68 days | Not available |
| Peduncle length | | |
| 1st lateral Salinas | 10 to 13 cm | 10 to 15 cm |
| 4th lateral Salinas | 13 to 15 cm | 15 to 20 cm |
| 1st lateral Bogotá | 10 to 15 cm | Not available |
| 4th lateral Bogotá | 15 to 20 cm | Not available |

What is claimed is:

1. A new and distinct Chrysanthemum plant named Arabella, as described and illustrated.

* * * * *

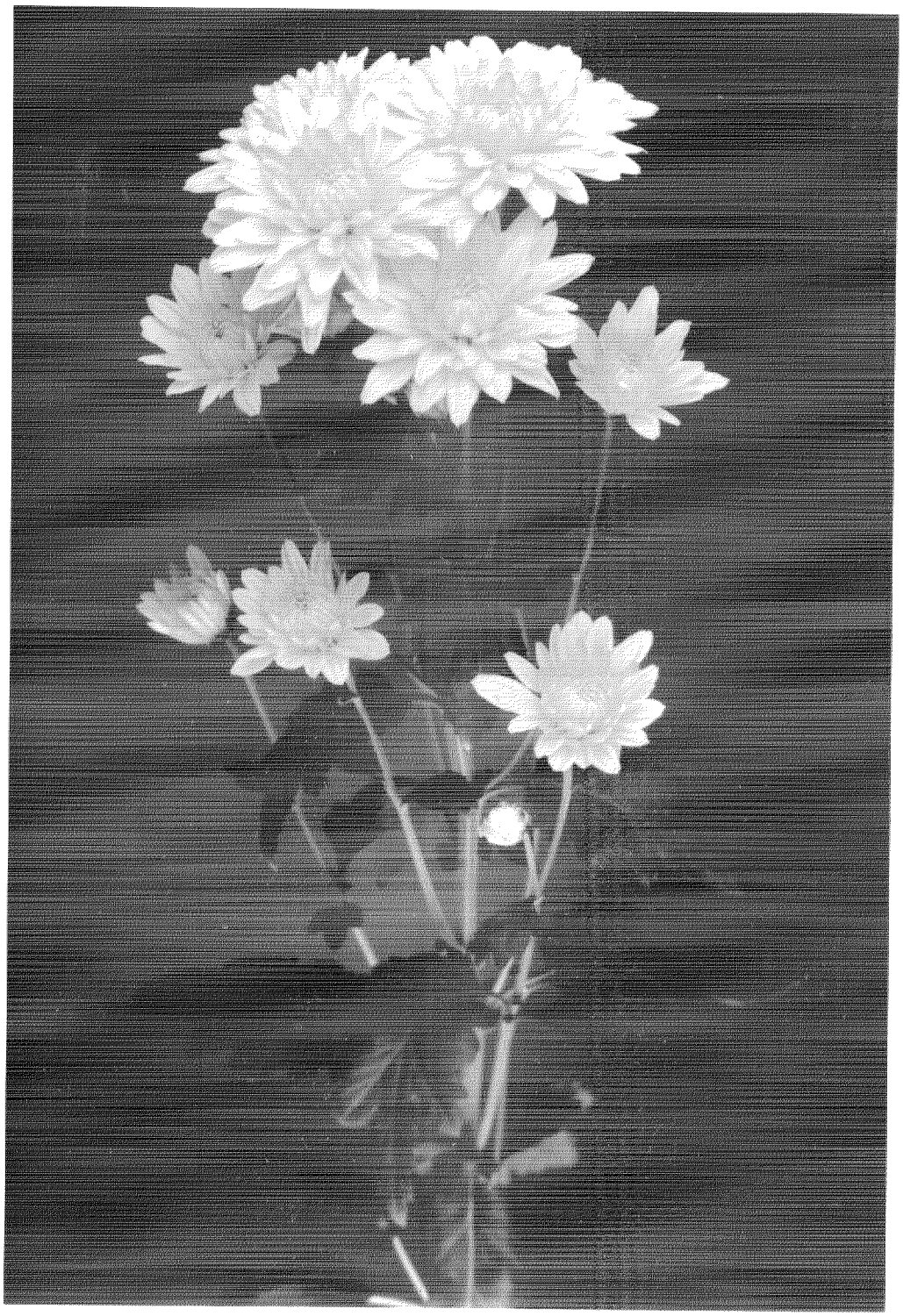

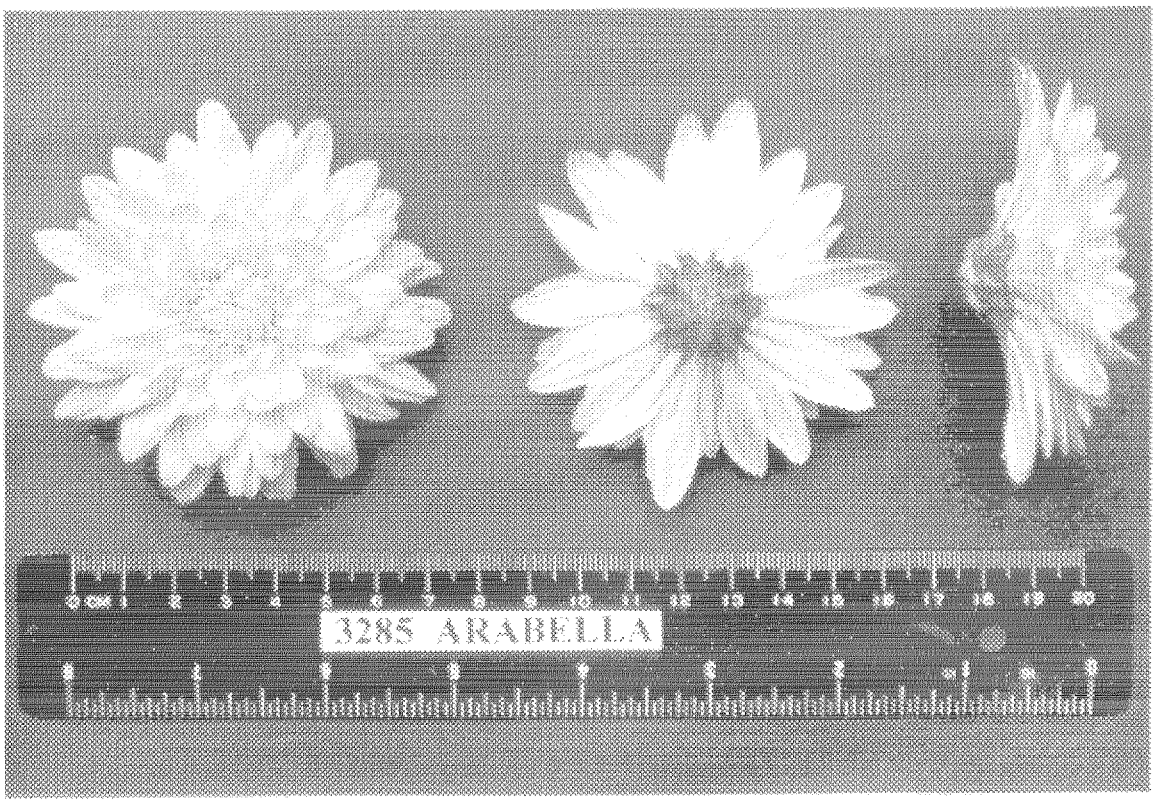
3285 ARABELLA

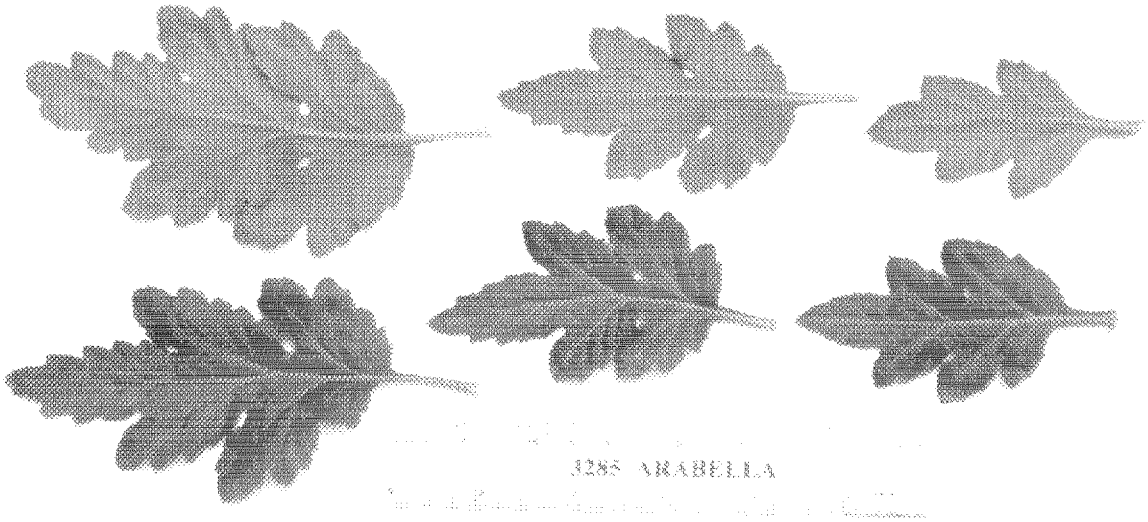
3285 ARABELLA